United States Patent [19]
Abbott et al.

[11] Patent Number: 5,654,251
[45] Date of Patent: Aug. 5, 1997

[54] ISOPARAFFIN-OLEFIN ALKYLATION

[75] Inventors: Ronald G. Abbott, Kingwood, Tex.; Ralph P. Williams, Bartlesville, Okla.; Marvin M. Johnson, Bartlesville, Okla.; John W. Vanderveen, Bartlesville, Okla.

[73] Assignee: Phillips Petroleum Company, Bartlesville, Okla.

[21] Appl. No.: 458,542

[22] Filed: Jun. 2, 1995

Related U.S. Application Data

[62] Division of Ser. No. 155,266, Nov. 22, 1993, which is a division of Ser. No. 75,427, Jun. 14, 1993, which is a continuation-in-part of Ser. No. 877,338, May 1, 1992, abandoned.

[51] Int. Cl.$^6$ ............................................ B01J 27/02
[52] U.S. Cl. ..................... 502/216; 502/224; 585/724; 585/730
[58] Field of Search ........................... 585/724, 730; 502/216, 168, 169, 224

[56] References Cited

U.S. PATENT DOCUMENTS

| | | | |
|---|---|---|---|
| 3,795,712 | 3/1974 | Torck et al. | 585/724 |
| 3,862,258 | 1/1975 | Huang et al. | 260/683.44 |
| 3,951,762 | 4/1976 | Voss et al. | 204/59 F |
| 4,024,203 | 5/1977 | Torck et al. | 585/724 |
| 4,058,575 | 11/1977 | Cahn et al. | 260/666 P |
| 4,069,268 | 1/1978 | Siskin et al. | 260/666 P |
| 4,094,924 | 6/1978 | Siskin et al. | 260/683.53 |
| 4,120,912 | 10/1978 | Hulme | 260/683.47 |
| 4,311,866 | 6/1982 | Chapman | 585/719 |
| 4,383,977 | 5/1983 | Hutson, Jr. et al. | 422/235 |
| 5,191,150 | 3/1993 | Child et al. | 585/809 |
| 5,262,652 | 11/1993 | Child et al. | 585/802 |
| 5,292,982 | 3/1994 | Del Rossi et al. | 585/724 |

*Primary Examiner*—Michael Lewis
*Assistant Examiner*—Thomas G. Dunn, Jr.
*Attorney, Agent, or Firm*—Charles W. Stewart

[57] ABSTRACT

A novel alkylation catalyst is described which is used in processes for alkylating olefin hydrocarbons with isoparaffin hydrocarbons to produce high octane alkylate products suitable for use as a blending component of gasoline motor fuel. The novel catalyst comprises a mixture of a hydrogen halide and a sulfone. The novel alkylation catalyst is utilized in a novel process for alkylating olefin hydrocarbons with isoparaffin hydrocarbons.

12 Claims, 6 Drawing Sheets

ISOPARAFFIN-OLEFIN ALKYLATION

This is a division of application Ser. No. 08/155,266, filed Nov. 22, 1993, which is a division of application Ser. No. 08/075,427, filed Jun. 14, 1993, which is a continuation-in-part of application Ser. No. 07/877,338, filed May 1, 1992, now abandoned.

The present invention relates to a hydrocarbon conversion process and a catalyst composition to be utilized in said hydrocarbon conversion process. More particularly, the invention relates to an improved alkylation process for the production of an alkylate product by contacting hydrocarbon with a novel catalyst composition.

The use of catalytic alkylation processes to produce branched hydrocarbons having properties that are suitable for use as gasoline blending components is well known in the art. Generally, the alkylation of olefins by saturated hydrocarbons, such as isoparaffins, is accomplished by contacting the reactants with an acid catalyst to form a reaction mixture, settling said mixture to separate the catalyst from the hydrocarbons, and further separating the hydrocarbons, for example, by fractionation, to recover the alkylation reaction product. Normally, the alkylation reaction product is referred to as "alkylate", and it preferably contains hydrocarbons having seven to nine carbon atoms. In order to have the highest quality gasoline blending stock, it is preferred that the hydrocarbons formed in the alkylation process be highly branched.

One of the more desirable alkylation catalysts is hydrofluoric acid, however, the use of hydrofluoric acid as an alkylation catalyst has certain drawbacks. One of the primary problems with the use of hydrofluoric acid as an alkylation catalyst is that it is a highly corrosive substance and it is toxic to human beings. The toxicity of hydrofluoric acid to human beings is further complicated by the fact that anhydrous hydrofluoric acid is typically a gas at normal atmospheric conditions of one atmosphere of pressure and 70° F. It is possible for the vapor pressure of hydrofluoric acid at standard atmospheric conditions to create certain safety concerns when it is exposed to the atmosphere. These safety concerns are created by the ease with which hydrofluoric acid is vaporized and released into the atmosphere.

In spite of the potential problems with human toxicity and the corrosive characteristics of hydrofluoric acid, industry has in the past determined that the benefits from the use of hydrofluoric acid as an alkylation catalyst outweigh the potential problems. For instance, hydrofluoric acid is an extremely effective alkylation catalyst in that it permits the reaction of olefins by isoparaffins at low process pressures and process temperatures. HF is particularly suited for use as a catalyst in the alkylation of butylenes and, in the case of the alkylation of propylene and amylenes, HF has been used as an effective catalyst whereas other alkylation catalysts, such as sulfuric acid, have been found to be not as effective in such alkylation services. Additionally, the alkylate formed from a hydrofluoric acid alkylation process is of a very high quality having such desirable properties as being a mixture of highly branched hydrocarbon compounds that provide a high octane motor fuel. Generally, it has been found that the alkylate produced by a hydrofluoric acid alkylation process has a higher octane value than that produced by typical sulfuric acid alkylation processes. Thus, it would be desirable to use an alkylation catalyst that has the desirable features of hydrofluoric acid catalyst but without having its high vapor pressure.

It is, therefore, an object of this invention to provide a novel alkylation catalyst having the desirable property of yielding a high quality alkylate when utilized in the alkylation of olefins with paraffins but having a lower vapor pressure than that of hydrofluoric acid.

A further object of this invention is to provide a process for the alkylation of olefins with paraffins in the presence of an alkylation catalyst having the desirable property of having a reduced vapor pressure but which produces a high quality alkylate product.

Thus, the process of the present invention relates to the alkylation of a hydrocarbon mixture comprising olefins and paraffins with a catalyst composition comprising the components of a hydrogen halide and a sulfone, wherein the sulfone component is present in said catalyst composition in an amount less than about 50 weight percent of the total weight of said composition and wherein the weight ratio of hydrogen halide to sulfone is at least 1:1.

The composition of the present invention comprises the components of a hydrogen halide and a sulfone, wherein said sulfone component is present in said composition in an amount less than about 50 weight percent of the total weight of said composition and wherein the weight ratio of hydrogen halide to sulfone is at least 1:1.

Other objects and advantages of the invention will be apparent from the foregoing detailed description of the invention, the appended claims and the drawings.

The novel composition of the present invention is suitable for use as an alkylation catalyst and can comprise, consist of, or consist essentially of a hydrogen halide component and a sulfone component. The term "consisting essentially of" as used herein when referring to the alkylation catalyst composition is intended to mean that the composition contains nothing, in addition to the requisite amount of hydrogen halide component and sulfone component, which would have a substantial adverse effect on the ability of the composition to act as a catalyst in an alkylation reaction.

The hydrogen halide component of the catalyst composition or catalyst mixture can be selected from the group of compounds consisting of hydrogen fluoride (HF), hydrogen chloride (HCl), hydrogen bromide (HBr), and mixtures of two or more thereof. The preferred hydrogen halide component, however, is hydrogen fluoride, which can be utilized in the catalyst composition in anhydrous form, but, generally, the hydrogen fluoride component utilized can have a small amount of water. The amount of water present in the hydrogen fluoride and sulfolane mixture in no event can be more than about 30 weight percent of the total weight of the hydrogen fluoride component, which includes the water, and preferably, the amount of water present in the hydrogen fluoride component is less than about 10 weight percent. Most preferably, the amount of water present in the hydrogen fluoride component is less than 5 weight percent. When referring herein to the hydrogen halide component, or more specifically to the hydrogen fluoride component, of the catalyst composition of the invention, it should be understood that these terms mean either the hydrogen halide component as an anhydrous mixture or a mixture that includes water. The references herein to weight percent water contained in the hydrogen halide component means the ratio of the weight of water to the sum weight of the water and hydrogen halide multiplied by a factor of 100 to place the weight ratio in terms of percent.

The sulfone component is an important and critical component of the catalyst composition because of the several functions it serves and because of the unexpected physical properties that it imparts to the catalyst composition. One important function of the presence of the sulfone component in the composition is its vapor pressure depressant effect upon the overall catalyst composition. It is an essential aspect of this invention for the sulfone component to be soluble in the hydrogen halide component and for the sulfone component to be essentially immiscible with olefin and paraffin hydrocarbons so as to permit easy separation of the hydrocarbons from the catalyst composition. Also, it is essential for the presence of the sulfone component to have a minimal impact upon an alkylation reaction selectivity and activity.

Generally, those skilled in the art of hydrogen fluoride catalyzed olefin alkylation processing have known that to obtain the highest quality of alkylate from the aforementioned olefin alkylation process, it is essential for the hydrogen fluoride catalyst to be as free from contaminating compounds as is feasible. It is generally known that small amounts of other compounds contained in the hydrogen fluoride catalyst of an olefin alkylation process can have detrimental effects upon product alkylate quality by negatively affecting the selectivity of the alkylation reaction toward the production of more desirable end-product, such as, for example, trimethylpentanes (TMP) in the case of the alkylation of butylenes by isobutane. It is further known to those skilled in the art that small amounts of components contained in a hydrogen fluoride alkylation catalyst can have a negative impact upon its activity toward the alkylation of olefins. Based upon the known effects of hydrogen fluoride catalyst contaminants upon the activity and selectivity of the alkylation process toward the production of high quality alkylate, one skilled in the art would expect that the addition of small to large amounts of a sulfone compound to a hydrogen fluoride catalyst would have an enormously detrimental effect upon its catalytic performance. However, it has been discovered that the presence of small quantities of a sulfone compound in combination with hydrogen fluoride will have little negative impact on the performance of the resultant mixture as an alkylation catalyst, but, it is further unexpected that instead of having a detrimental impact upon the catalytic performance, a small concentration in an amount less than about 30 weight percent of a sulfone component in combination with the hydrogen fluoride can enhance the performance of the resultant composition as an alkylation process catalyst. Therefore, to take advantage of the vapor pressure depressant effects of the sulfone compound, it is desirable to utilize the sulfone in the catalyst mixture in an amount in the range of from about 2.5 weight percent to about 50 weight percent. A concentration of the sulfone in the catalyst mixture exceeding 50 weight percent has such a significantly negative impact upon alkylate quality when the composition is utilized as an alkylation reaction catalyst that the composition becomes ineffective as a catalyst. Thus, 50 weight percent sulfone in the catalyst mixture becomes a critical upper limit for the sulfone compound. In the situation where both vapor pressure depression and improved catalytic activity and selectivity are desired, the composition that works best in the alkylation of olefins has less than 30 weight percent sulfone. To achieve optimal benefits from the catalyst composition, the preferred catalyst mixture should contain the sulfone component in the range of from about 5 weight percent to about 30 weight percent and, more preferably, the sulfone concentration shall range from 10 to 25 weight percent.

In addition to the above-described concentration ranges and limitations for the sulfone component of the catalyst mixture, it is essential, if not critical, for the weight ratio of the hydrogen halide to sulfone in the catalyst mixture to be at least about 1:1. The reason for such a minimum weight ratio of hydrogen halide to sulfone in the catalyst mixture is that the ratio of less than 1:1 has such a negative impact upon the alkylate quality when the catalyst composition is utilized as an alkylation reaction catalyst that composition becomes commercially ineffective as a catalyst. Therefore, a 1:1 weight ratio of hydrogen halide to sulfone in the catalyst mixture becomes a critical lower limit for this ratio.

The sulfones suitable for use in this invention are the sulfones of the general formula $$R-SO_2-R'$$

wherein R and R' are monovalent hydrocarbon alkyl or aryl substituents, each containing from 1 to 8 carbon atoms. Examples of such substituents include dimethylsulfone, di n-propylsulfone, diphenylsulfone, ethylmethylsulfone and the alicyclic sulfones wherein the $SO_2$ group is bonded to a hydrocarbon ring. In such a case, R and R' are forming together a branched or unbranched hydrocarbon divalent moiety preferably containing from 3 to 12 carbon atoms. Among the latter, tetramethylenesulfone or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as for example, chloromethylethylsulfone. These sulfones may advantageously be used in the form of mixtures.

This novel alkylation catalyst composition solves many of the problems that herebefore have been encountered in typical alkylation processes that use hydrofluoric acid as an alkylation catalyst. For instance, this novel catalyst composition has a significantly lower vapor pressure than that of the standard hydrofluoric acid alkylation catalyst. The advantage of using an alkylation catalyst having a much lower vapor pressure than that of hydrofluoric acid is that a lesser amount of the acid catalyst will vaporize and enter into the atmosphere in cases where the catalyst is exposed to the atmosphere. In particular, when making a comparison between the novel catalyst composition and hydrofluoric acid, one notices a significant difference in the vapor pressures of the two catalysts. The effect of the presence of sulfolane mixed with hydrogen fluoride is illustrated in the vapor pressure plot of FIG. 1. Since hydrofluoric acid has a substantial vapor pressure at typical atmospheric or ambient conditions, it is often in a vapor state at such conditions, and this vapor pressure makes it a possibly less controllable compound in cases where it is exposed to the environment.

The novel catalyst composition as described herein, solves many of the problems associated with the use of hydrofluoric acid as a catalyst since it provides the benefit of having a lower vapor pressure at ambient conditions than that of hydrofluoric acid. But, in addition to the benefit of having a lower vapor pressure at ambient conditions, the novel catalyst composition further can be utilized in typical alkylation processes to provide practical reaction rates at low operating pressures and low operating temperatures to produce a high quality alkylate product which is suitable for use as a blending component of gasoline motor fuel. A further benefit from the novel catalyst composition is that it is easier to handle commercially than hydrofluoric acid.

Figure 2:
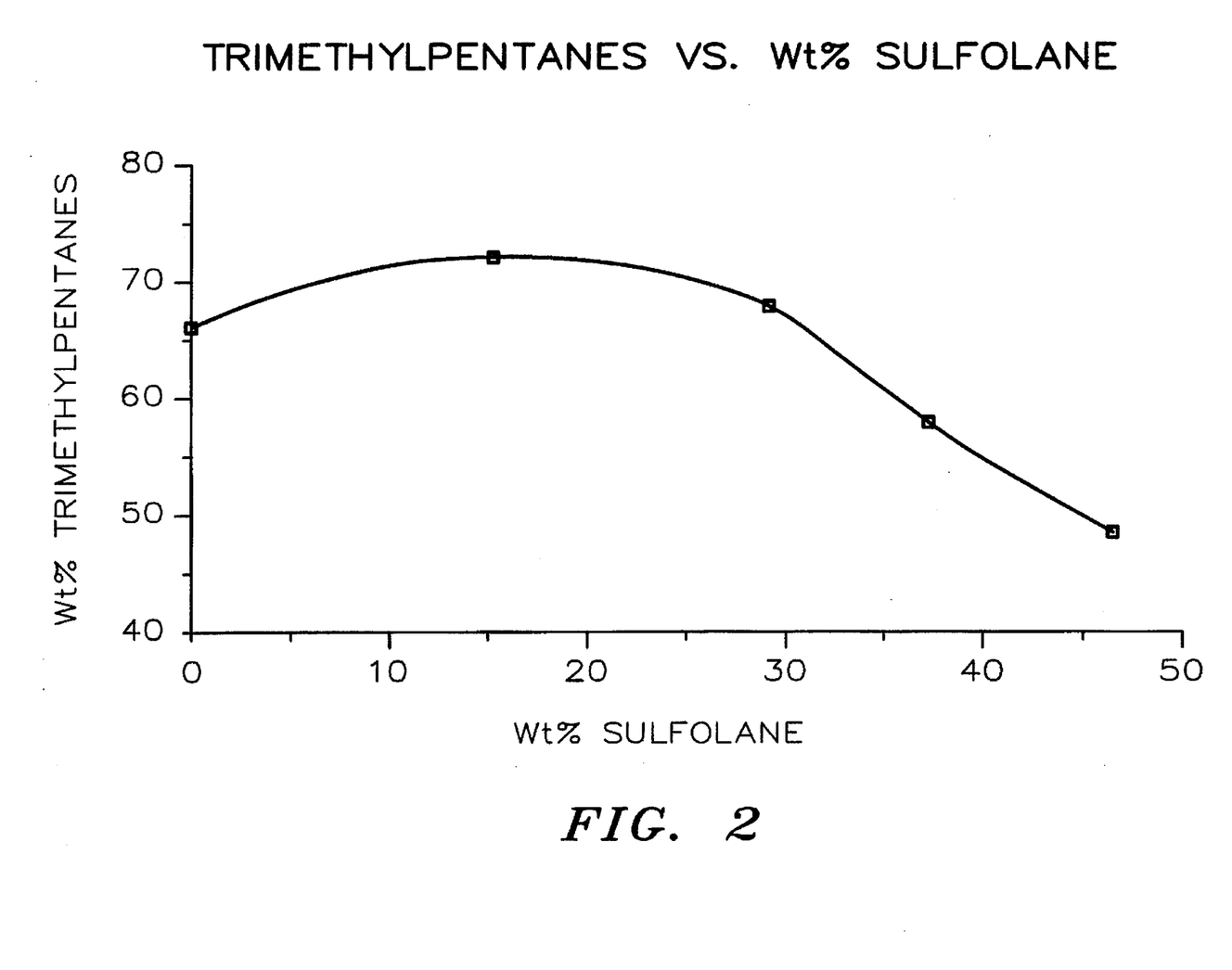
FIG. 2 is a graphical diagram comparing the selectivity of the process of alkylating butylenes by isobutane when the novel hydrogen fluoride and sulfolane catalyst mixture is utilized toward the production of trimethylpentane as a function of weight percent sulfolane in the catalyst mixture.
Figure 3:
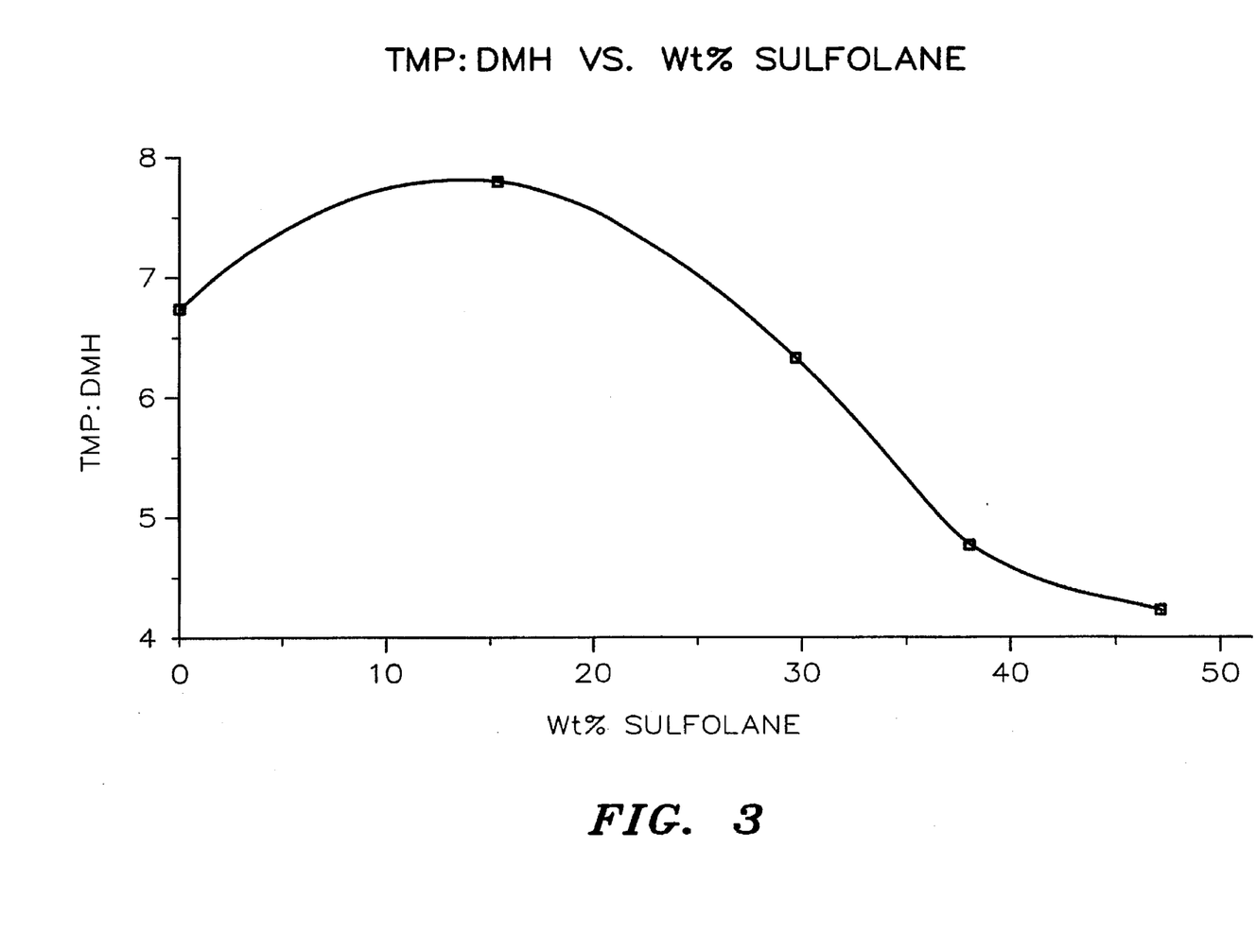
FIG. 3 is a graphical diagram comparing the ratio of trimethylpentane to dimethylhexane contained in the product of the alkylation process that uses the novel hydrogen fluoride and sulfolane catalyst mixture in the alkylation of butylenes by isobutane as a function of the weight percent sulfolane in the catalyst mixture.
Figure 4:
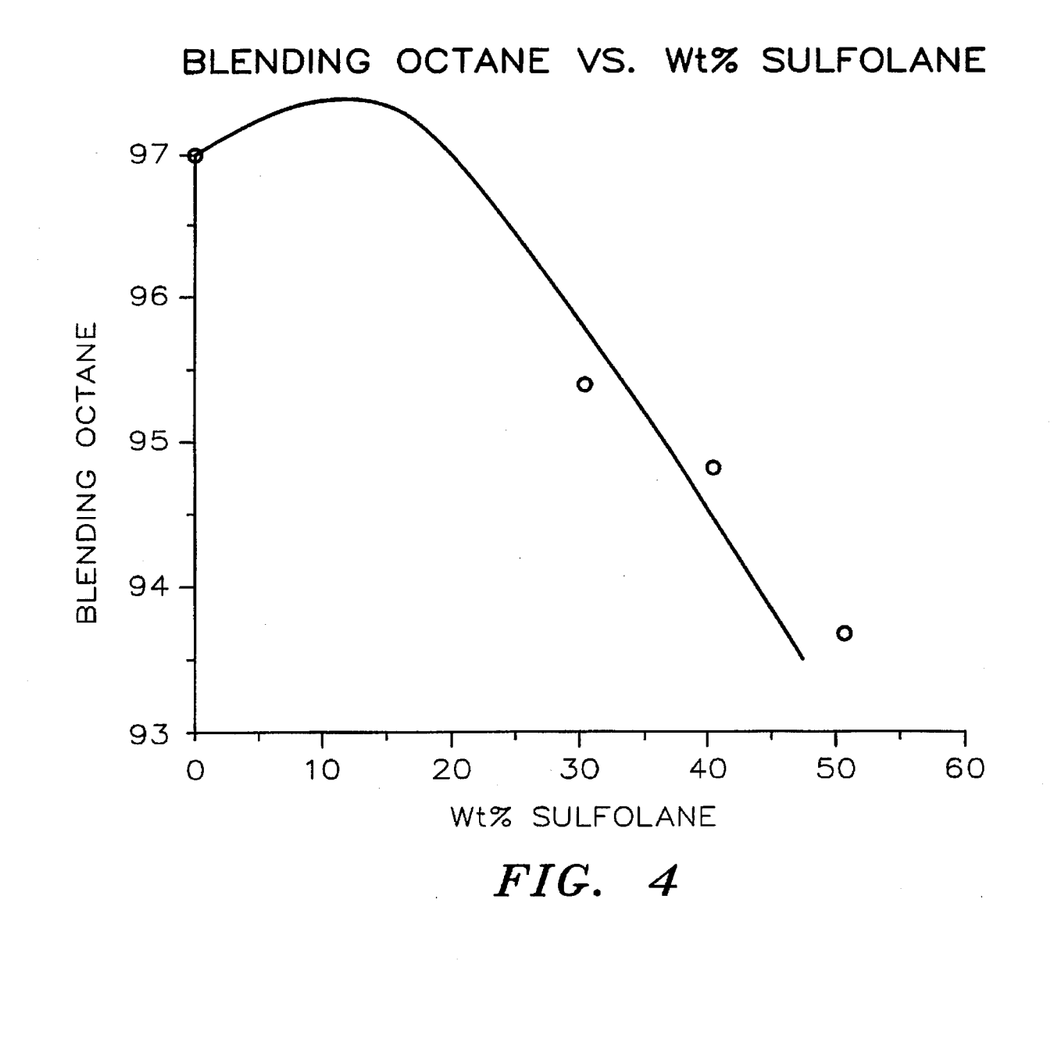
FIG. 4 is a graphical diagram comparing the octane of the product of the alkylation process that uses the novel hydrogen fluoride and sulfolane catalyst mixture in the alkylation of butylenes by isobutane as a function of the weight percent sulfolane in the catalyst mixture.

The benefits from the use of a hydrogen fluoride and sulfone catalyst mixture is also illustrated in FIGS. 2, 3 and 4 in which is shown the alkylate product quality that results from utilizing the novel hydrogen fluoride and sulfone co-mixture to catalyze the reaction of mono-olefin hydrocarbons by isoparaffins. As can be seen from FIG. 2, the total amount of the more desirable alkylate product of trimethylpentane produced in the alkylation reaction of butylenes with isobutane increases with increases in the amount of sulfolane present in the alkylation catalyst mixture up to an optimum range of about 10 weight percent sulfolane to about 25 weight percent sulfolane. Also, it is shown in FIG. 2 that there is a maximum amount of sulfolane present in the catalyst mixture at which point the alkylate quality becomes so undesirable that the hydrogen fluoride and sulfolane mixture becomes ineffective as a catalyst. Based on the data presented herein and in FIGS. 2, 3 and 4, it is believed that the critical upper limit for the amount of sulfolane contained in the hydrofluoride and sulfolane catalyst mixture is about 50 weight percent.

Alkylation processes contemplated in the present invention are those liquid phase processes wherein mono-olefin hydrocarbons such as propylene, butylenes, pentylenes, hexylenes, heptylenes, octylenes and the like are alkylated by isoparaffin hydrocarbons such as isobutane, isopentane, isohexane, isoheptane, isooctane and the like for production of high octane alkylate hydrocarbons boiling in the gasoline range and which are suitable for use in gasoline motor fuel. Preferably, isobutane is selected as the isoparaffin reactant and the olefin reactant is selected from propylene, butylenes, pentylenes and mixtures thereof for production of an alkylate hydrocarbon product comprising a major portion of highly branched, high octane value aliphatic hydrocarbons having at least seven carbon atoms and less than ten carbon atoms.

In order to improve selectivity of the alkylation reaction toward the production of the desirable highly branched aliphatic hydrocarbons having seven or more carbon atoms, a substantial stoichiometric excess of isoparaffin hydrocarbon is desirable in the reaction zone. Molar ratios of isoparaffin hydrocarbon to olefin hydrocarbon of from about 2:1 to about 25:1 are contemplated in the present invention. Preferably, the molar ratio of isoparaffin-to-olefin will range from about 5 to about 20; and, most preferably, it shall range from 8 to 15. It is emphasized, however, that the above recited ranges for the molar ratio of isoparaffin-to-olefin are those which have been found to be commercially practical operating ranges; but, generally, the greater the isoparaffin-to-olefin ratio in an alkylation reaction, the better the resultant alkylate quality.

Isoparaffin and olefin reactant hydrocarbons normally employed in commercial alkylation processes are derived from refinery process streams and usually contain small amounts of impurities such as normal butane, propane, ethane and the like. Such impurities are undesirable in large concentrations as they dilute reactants in the reaction zone, thus decreasing reactor capacity available for the desired reactants and interfering with good contact of isoparaffin with olefin reactants. Additionally, in continuous alkylation processes wherein excess isoparaffin hydrocarbon is recovered from an alkylation reaction effluent and recycled for contact with additional olefin hydrocarbon, such nonreactive normal paraffin impurities tend to accumulate in the alkylation system. Consequently, process charge streams and/or recycle streams which contain substantial amounts of normal paraffin impurities are usually fractionated to remove such impurities and maintain their concentration at a low level, preferably less than about 5 volume percent, in the alkylation process.

Alkylation reaction temperatures within the contemplation of the present invention are in the range of from about 0° F. to about 150° F. Lower temperatures favor alkylation reaction of isoparaffin with olefin over competing olefin side reactions such as polymerization. However, overall reaction rates decrease with decreasing temperatures. Temperatures within the given range, and preferably in the range from about 30° F. to about 130° F., provide good selectivity for alkylation of isoparaffin with olefin at commercially attractive reaction rates. Most preferably, however, the alkylation temperature should range from 50° F. to 100° F.

Reaction pressures contemplated in the present invention may range from pressures sufficient to maintain reactants in the liquid phase to about fifteen (15) atmospheres of pressure. Reactant hydrocarbons may be normally gaseous at alkylation reaction temperatures, thus reaction pressures in the range of from about 40 pounds gauge pressure per square inch (psig) to about 160 psig are preferred. With all reactants in the liquid phase, increased pressure has no significant effect upon the alkylation reaction.

Contact times for hydrocarbon reactants in an alkylation reaction zone, in the presence of the alkylation catalyst of the present invention generally should be sufficient to provide for essentially complete conversion of olefin reactant in the alkylation zone. Preferably, the contact time is in the range from about 0.05 minute to about 60 minutes. In the alkylation process of the present invention, employing isoparaffin-to-olefin molar ratios in the range of about 2:1 to about 25:1, wherein the alkylation reaction mixture comprises about 40–90 volume percent catalyst phase and about 60–10 volume percent hydrocarbon phase, and wherein good contact of olefin with isoparaffin is maintained in the reaction zone, essentially complete conversion of olefin may be obtained at olefin space velocities in the range of about 0.1 to about 200 volumes olefin per hour per volume catalyst (v/v/hr.). Optimum space velocities will depend upon the type of isoparaffin and olefin reactants utilized, the particular compositions of alkylation catalyst, and the alkylation reaction conditions. Consequently, the preferred contact times are sufficient for providing an olefin space velocity in the range of about 0.1 to about 200 (v/v/hr.) and allowing essentially complete conversion of olefin reactant in the alkylation zone.

The process may be carried out either as a batch or continuous type of operation, although it is preferred for economic reasons to carry out the process continuously. It has been generally established that in alkylation processes, the more intimate the contact between the feedstock and the catalyst the better the quality of alkylate product obtained. With this in mind, the present process, when operated as a batch operation, is characterized by the use of vigorous mechanical stirring or shaking of the reactants and catalyst.

In continuous operations, in one embodiment, reactants may be maintained at sufficient pressures and temperatures to maintain them substantially in the liquid phase and then continuously forced through dispersion devices into the reaction zone. The dispersion devices can be jets, nozzles, porous thimbles and the like. The reactants are subsequently mixed with the catalyst by conventional mixing means such as mechanical agitators or turbulence of the flow system. After a sufficient time, the product can then be continuously separated from the catalyst and withdrawn from the reaction system while the partially spent catalyst is recycled to the reactor. If desired, a portion of the catalyst can be continuously regenerated or reactivated by any suitable treatment and returned to the alkylation reactor.

The following examples demonstrate the advantages of the present invention. These examples are by way of illustration only, and are not intended as limitations upon the invention as set out in the appended claims.

EXAMPLE I

This example describes the experimental method used to determine the vapor pressure of various hydrogen fluoride and sulfolane mixtures and to present vapor pressure data for such mixtures demonstrating the effectiveness of sulfolane as a vapor pressure depressant.

Figure 1:
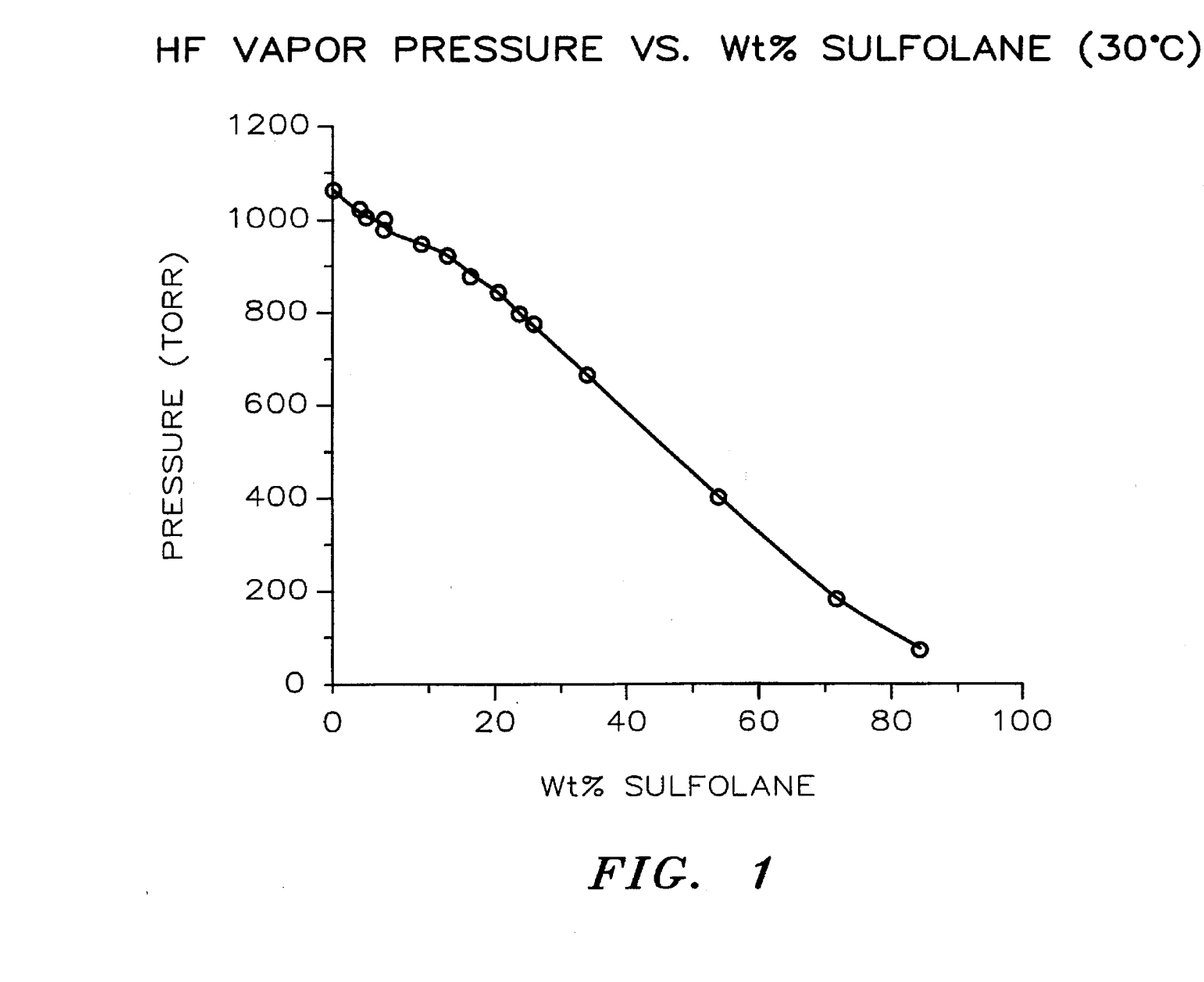
FIG. 1 is a graphical diagram illustrating at a given temperature the change in vapor pressure of the novel hydrogen fluoride and sulfolane catalyst mixture as a function of the weight percent sulfolane in the catalyst mixture.

A 100 mL monel bomb was dried and evacuated, followed by the addition of a prescribed amount of anhydrous hydrogen fluoride. A specific amount of sulfolane was then added to the bomb. Once the bomb achieved the desired temperature, the pressure within the bomb was recorded. The vapor pressure was assumed to be that of HF vapor alone (sulfolane has a boiling point of 283° C.). FIG. 1 presents a portion of the vapor pressure data obtained by this experimental method and illustrates the change in vapor pressure of the novel hydrogen fluoride and sulfolane catalyst mixture as a function of the weight percent sulfolane in the catalyst mixture.

EXAMPLE II

This example describes the method which utilizes batch reactions to test the feasibility of using a hydrogen fluoride and sulfolane mixture as a catalyst for the alkylation of mono-olefins by isoparaffins. Data are presented to demonstrate the unexpectedly improved properties of the alkylate product from such a catalytic process and to demonstrate that for certain concentration ranges the catalyst mixture unexpectedly provides a good quality alkylate.

HF/sulfolane mixtures were evaluated for alkylation performance in batch reactions at 90° F. In a typical trial, the desired amount of sulfolane was added to a 300 mL monel autoclave under a blanket of nitrogen. Anhydrous HF was then introduced into the autoclave and heated to 90° F. with stirring at 500 RPM. The stirring was then increased to 2500 RPM, and an 8.5:1 isobutane:2-butenes mixture was added with nitrogen backpressure at a rate of 100 mL/min. at a pressure of 150–200 psig. After 5 minutes, the stirring was stopped, followed by the transfer of the reactor contents to a Jerguson gauge for phase separation. The hydrocarbon product was then characterized by gas chromatography.

The data presented in Table I were obtained by using the experimental method described in this Example II. FIGS. 2 and 3 are graphical representations of this data. FIG. 2 compares the selectivity of the alkylation process toward the production of the highly desirable trimethylpentanes as a function of weight percent sulfolane in the catalyst mixture. FIG. 3 compares the ratio of trimethylpentanes to dimethylhexanes contained in the alkylation product as a function of the weight percent sulfolane in the catalyst mixture.

TABLE I

Batch Results, Anhydrous HF/Sulfolane

| | Test Samples | | | | | |
|---|---|---|---|---|---|---|
| | No. 1 | No. 2 | No. 3 | No. 4 | No. 5 | No. 6 |
| mL sulfolane | 0.00 | 13.00 | 28.00 | 38.00 | 50.00 | 50.00 |
| mL HF | 100.00 | 93.50 | 86.00 | 81.00 | 75.00 | 50.00 |
| mL Feed | 100.00 | 93.50 | 86.00 | 81.00 | 75.00 | 100.00 |
| wt. % sulfolane | 0.00 | 15.09 | 29.39 | 37.49 | 46.02 | 56.11 |
| % TMP | 65.40 | 71.28 | 67.29 | 57.14 | 52.21 | 20.45 |
| % DMH | 9.63 | 9.02 | 10.52 | 11.90 | 12.28 | 1.58 |
| TMP:DMH | 6.79 | 7.90 | 6.40 | 4.80 | 4.25 | 12.97 |
| C9+ | 5.81 | 10.56 | 10.98 | 16.49 | 18.96 | 0.28 |
| Organic fluorides | 0.00 | 0.00 | 0.00 | 0.00 | 0.00 | 69.74 |

EXAMPLE III

This example describes the steady state evaluation method for testing the feasibility of using a hydrogen fluoride and sulfolane mixture as a catalyst for the alkylation of mono-olefins by isoparaffins. Data are presented to demonstrate that for certain concentration ranges the catalyst mixture unexpectedly provides a good quality alkylate.

A reactor was constructed to enable steady state evaluation of HF/sulfolane alkylation catalysts using a 300 mL monel autoclave. A 10:1 isobutane:2-butenes feed was introduced into the autoclave with stirring at 2000 RPM at a rate of 600 mL/hour. The reactor effluent flowed into a monel Jerguson gauge for phase separation. The hydrocarbon phase was passed through alumina and collected, while the acid phase was recirculated to the reactor. Alkylate was evaluated by gas chromatography and by research and motor octane tests performed on test engines.

The data presented in Table II were obtained by using the experimental method described in this Example III. FIG. 4 is a graphical representation of some of the data provided in Table II and compares the octane of the alkylate product as a function of the weight percent sulfolane in the catalyst mixture. As is evident from the data presented in Table II, the alkylate quality degenerates at the point where the catalyst has a weight ratio of hydrogen fluoride to sulfolane of less than 1:1. This deterioration is demonstrated by that data presented which depicts alkylate quality measures such as the concentration of $C_8$ compounds, the ratio of TMP to DMH, the concentration of $C_9+$ compounds and the octane of the alkylate. As is shown in Table II, the concentration of $C_8$ compounds and the ratio of TMP to DMH begin to significantly decline when the alkylation catalyst has a ratio of hydrogen fluoride to sulfolane of less than 1:1. Also, the concentration of undesirable $C_9+$ compounds in the alkylate begins to significantly increase when a catalyst mixture having a ratio of hydrogen fluoride to sulfone is less than 1:1.

TABLE II

|  | 100% HF | 70/30 HF/ sulfolane | 60/40 HF/ sulfolane | 50/50 HF/ sulfolane | 40/60 HF/ sulfolane |
|---|---|---|---|---|---|
| C8 | 93.5 | 81.1 | 82.2 | 56.9 | 26.95 |
| TMP | 86.3 | 70.5 | 70.4 | 46.1 | 22.26 |
| DMH | 7.1 | 10.6 | 11.7 | 10.6 | 4.54 |
| TMP/DMH | 12.1 | 6.6 | 6.0 | 4.4 | 4.90 |
| C9+ | 3.4 | 3.9 | 8.1 | 23.1 | 36.32 |
| R + M/2 | 97.0 | 95.5 | 94.9 | 93.7 | NA |

EXAMPLE IV

This example describes the steady state evaluation method for testing the feasibility of using a hydrogen fluoride and sulfolane mixture as a catalyst for the alkylation of a typical refinery feed mixture of mono-olefins and isoparaffins (BB Feed). Data are presented to demonstrate that for certain concentration ranges the catalyst mixture unexpectedly provides a good quality alkylate.

A reactor was constructed to enable steady state evaluation of HF/sulfolane alkylation catalysts using a 300 mL monel autoclave. The feed mixture of olefins and paraffins presented in Table III was introduced into the autoclave with stirring at 2000 RPM at a rate of 600 mL/hour. The reactor effluent flowed into a monel Jerguson gauge for phase separation. The hydrocarbon phase was passed through alumina and collected, while the acid phase was recirculated to the reactor. Alkylate was evaluated by gas chromatography and the octane values (R+M/2) were calculated using the method for computing alkylate octane described in the publication authored by T. Hutson, Jr. and R. S. Logan in *Hydrocarbon Processing*, September 1975, pages 107–110. This published article is incorporated herein by reference.

TABLE III

| BB Feed | |
|---|---|
| Hydrocarbons | |
| Propylene | 0.000 |
| Propane | 0.569 |
| Isobutane | 88.027 |
| 1-butene | 2.818 |
| Isobutylene | 0.000 |
| 1,3-butadiene | 0.000 |
| n-butane | 3.505 |
| trans-2-butene | 1.716 |
| cis-2-butene | 1.236 |
| Isopentane | 1.008 |
| n-pentane | 0.728 |
| $C_5$ olefins | 0.393 |
|  | 100.000 |
| Oxygenates | |
| Acetone | 29 ppm |
| Dimethyl ether | 10 ppm |
| MTBE | 1 ppm |

Figure 5:
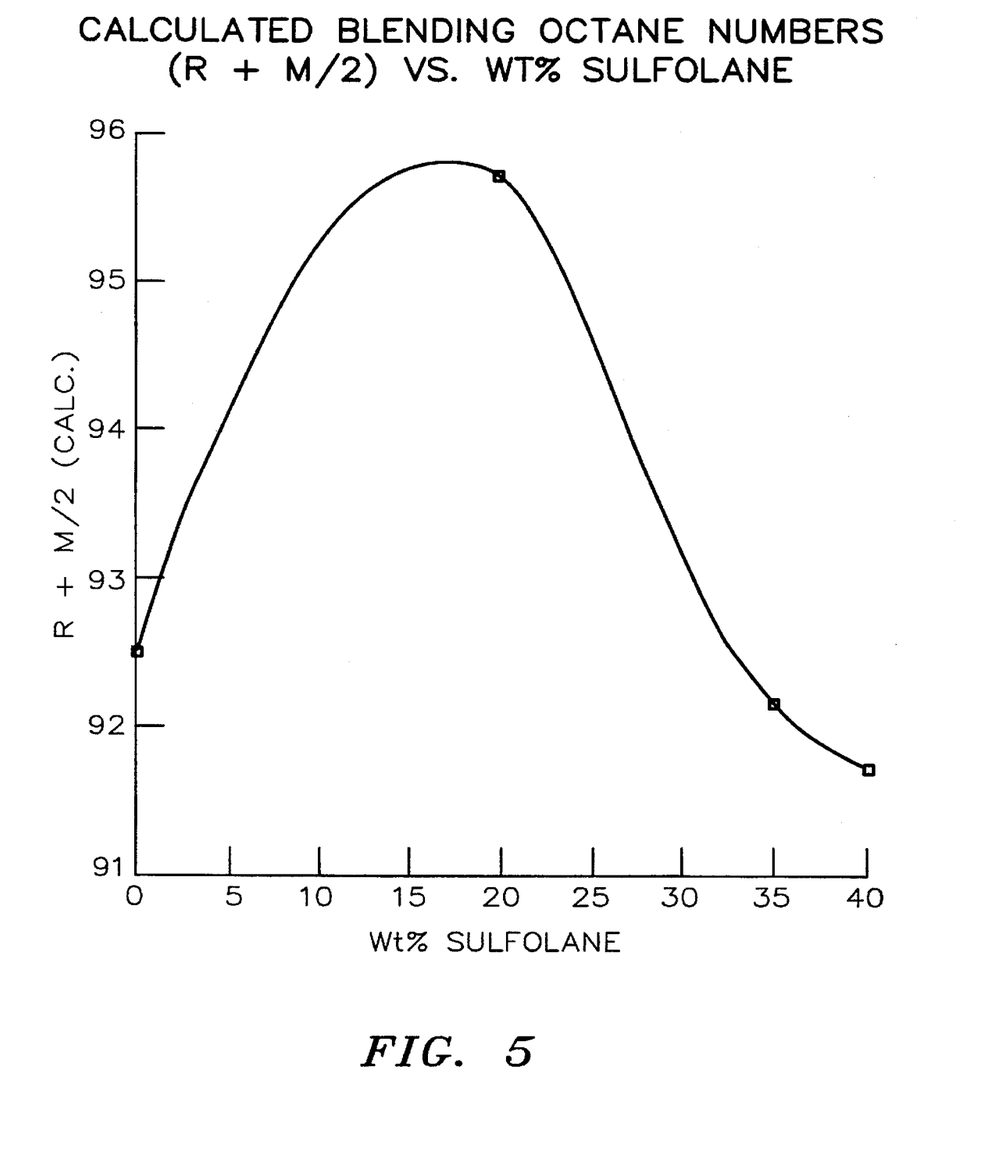
FIG. 5 is a graphical diagram comprising the calculated octane value of the product of the alkylation process, in which a representative refinery feed is processed, that uses the novel hydrogen fluoride and sulfolane catalyst mixture as a function of the weight percent sulfolane in the catalyst mixture.
Figure 6:
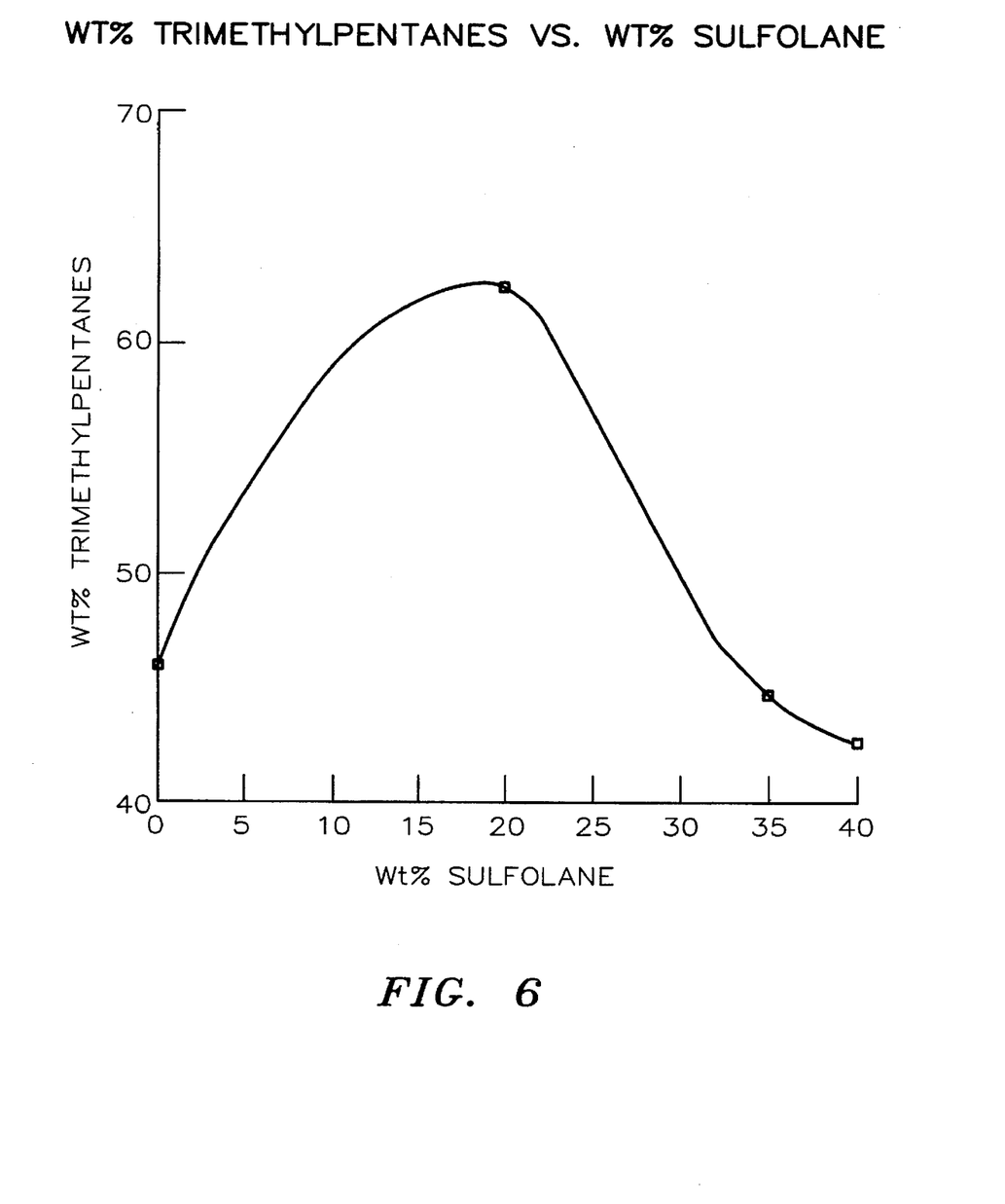
FIG. 6 is a graphical diagram comparing the selectivity of the alkylation process, in which a representative refinery feed is processed and the novel hydrogen fluoride and sulfolane catalyst mixture is utilized, toward the production of trimethylpentanes as a function of weight percent sulfolane in the catalyst mixture.

The data presented in Table IV was obtained by using the experimental method described in this Example IV. FIG. 5 is a graphical representation of some of the data provided in Table IV and compares the calculated octane value of the alkylate product as a function of the weight percent sulfolane in the catalyst mixture. FIG. 6 compares the selectivity of the alkylation process, in which a BB feed is processed, toward the production of the highly desirable trimethylpentanes as a function of weight percent sulfolane in the catalyst mixture.

TABLE IV

|  | 100% HF | 98/2 HF/Water | 80/20 HF/ sulfolane | 65/35 HF/ sulfolane | 60/40 HF/ sulfolane |
|---|---|---|---|---|---|
| Hours | 17 Hrs | 13 Hrs | 20 Hrs | 7 Hrs | 11 Hrs |
| $C_8$ | 56.9 | 59.2 | 73.2 | 55.8 | 51.8 |
| TMP | 45.9 | 50.9 | 62.4 | 44.6 | 42.5 |
| DMH | 11.0 | 8.3 | 10.8 | 6.9 | 9.0 |
| TMP/DMH | 4.2 | 6.1 | 5.8 | 6.5 | 4.7 |
| $C_9+$ | 3.9 | 2.6 | 4.2 | 11.4 | 6.8 |
| (R + M)/2 (calculated) | 92.5 | 94.2 | 95.7 | 92.1 | 91.7 |

While this invention has been described in terms of the presently preferred embodiment, reasonable variations and modifications are possible by those skilled in the art. Such variations and modifications are within the scope of the described invention and the appended claims.

That which is claimed is:

1. A method for decreasing the rate of vaporization of hydrogen fluoride from a catalyst mixture containing hydrogen fluoride when said catalyst mixture is released into the atmosphere from a process system, said method comprising admixing a vapor pressure depressant amount of a sulfone to said catalyst mixture to thereby form an admixture wherein said vapor pressure depressant amount of said sulfone is such that the weight ratio of hydrogen fluoride to sulfone in said admixture is at least 1:1 and the amount of sulfone in said admixture is in the range of from about 2.5 weight percent to 50 weight percent; and releasing said admixture into the atmosphere from said process system.

2. A method as recited in claim 1 wherein said vapor pressure depressant amount of said sulfone in said admixture is in the range of from about 5 weight percent to about 30 weight percent.

3. A method as recited in claim 2 wherein said vapor pressure depressant amount of said sulfone in said admixture is in the range of from about 10 weight percent to about 25 weight percent.

4. A method as recited in claim 1 wherein said sulfone is sulfolane.

5. A method as recited in claim 2 wherein said sulfone is sulfolane.

6. A method as recited in claim 3 wherein said sulfone is sulfolane.

7. A method for decreasing the rate of vaporization of hydrogen fluoride from a catalyst mixture containing hydrogen fluoride when said catalyst mixture is released into the atmosphere from a process system, said method comprising admixing a sulfone with said catalyst mixture in an amount so as to give a concentration of sulfone in said catalyst mixture in the range of from about 2.5 weight percent to 50 weight percent and a weight ratio of hydrogen fluoride to sulfone in said catalyst mixture of at least 1:1; and releasing said catalyst mixture into the atmosphere from said process system.

8. A method as recited in claim 7 wherein said concentration of sulfone in said catalyst mixture is in the range of from about 5 weight percent to about 30 weight percent.

9. A method as recited in claim 7 wherein said concentration of sulfone in said catalyst mixture is in the range of from about 10 weight percent to about 25 weight percent.

10. A method as recited in claim 7 wherein said sulfone is sulfolane.

11. A method as recited in claim 8 wherein said sulfone is sulfolane.

12. A method as recited in claim 9 wherein said sulfone is sulfolane.

* * * * *